(12) United States Patent
Dmitrieva et al.

(10) Patent No.: US 11,219,427 B2
(45) Date of Patent: Jan. 11, 2022

(54) ULTRASOUND SYSTEM AND METHOD FOR BREAST TISSUE IMAGING AND ANNOTATION OF BREAST ULTRASOUND IMAGES

(71) Applicant: KONINKLIJKE PHILIPS N.V., Eindhoven (NL)

(72) Inventors: Julia Dmitrieva, Bothell, WA (US); Gary Cheng-How Ng, Redmond, WA (US); James Robertson Jago, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 425 days.

(21) Appl. No.: 16/306,870

(22) PCT Filed: Jun. 7, 2017

(86) PCT No.: PCT/EP2017/063874
§ 371 (c)(1),
(2) Date: Dec. 3, 2018

(87) PCT Pub. No.: WO2017/211910
PCT Pub. Date: Dec. 14, 2017

(65) Prior Publication Data
US 2021/0030392 A1    Feb. 4, 2021

Related U.S. Application Data

(60) Provisional application No. 62/346,641, filed on Jun. 7, 2016.

(51) Int. Cl.
*A61B 8/08* (2006.01)
*A61B 8/00* (2006.01)

(52) U.S. Cl.
CPC .......... *A61B 8/0825* (2013.01); *A61B 8/4245* (2013.01); *A61B 8/463* (2013.01); *A61B 8/468* (2013.01); *A61B 8/469* (2013.01)

(58) Field of Classification Search
CPC ..... A61B 8/0825; A61B 8/4245; A61B 8/463; A61B 8/468; A61B 8/469; A61B 8/00
See application file for complete search history.

(56) References Cited

U.S. PATENT DOCUMENTS 5,709,206 A   1/1998   Teboul
7,124,760 B2  10/2006  Wong
(Continued)

FOREIGN PATENT DOCUMENTS

WO   2006038182 A1   4/2006
WO   2014206881 A1   12/2014

OTHER PUBLICATIONS

Park, et al., "Sonographic Detection of Multifocality in Breast Carcinoma", Journal of Clinical Ultrasound, vol. 31, No. 6, Jul./Aug. 2003, pp. 293-298.

(Continued)

*Primary Examiner* — Pascal M Bui Pho
*Assistant Examiner* — Adil Partap S Virk

(57) ABSTRACT

The present disclosure describes ultrasound imaging systems and methods that may be used to image breast tissue. An ultrasound imaging system according to one embodiment may include a user interface comprising a display, a processor operatively connected to the user interface, and memory comprising processor-executable instructions, which when executed by the processor cause the user interface to display a first ultrasound image of a breast on the display and receive an indication of a first region of interest (ROI) in the first ultrasound image. The memory may include instructions to further cause the user interface to display a second ultrasound image of the breast on the display and receive an indication of a second region of interest in the second ultrasound image. The processor may be configured to determine locations of the first and second regions of interest based on probe position data associated with the first and second images, respectively and cause the user interface to display a visual indication of a relative (Continued)

distance between the first and second regions of interest if the relative distance is less than or equal to a predetermined amount.

28 Claims, 8 Drawing Sheets

(56) References Cited

U.S. PATENT DOCUMENTS

| | | | |
|---|---|---|---|
| 8,064,677 B2 | 11/2011 | Nie et al. | |
| 2003/0007598 A1* | 1/2003 | Wang | A61B 8/5238 378/37 |
| 2009/0306514 A1* | 12/2009 | Imamura | A61B 8/461 600/458 |
| 2010/0040274 A1* | 2/2010 | Zhang | A61B 8/0825 382/131 |
| 2012/0176365 A1* | 7/2012 | Hansegard | A61B 8/469 345/419 |
| 2015/0182191 A1* | 7/2015 | Caluser | A61B 8/5246 600/440 |
| 2017/0281131 A1* | 10/2017 | Sendai | A61B 8/4416 |

OTHER PUBLICATIONS

Wilkinson, et al., "Increasing the diagnosis of multifocal primary breast cancer by the use of bilateral whole-breast ultrasound", Clinical Radiology (2005), vol. 60, No. 5, May 1, 2005, pp. 573-578.

* cited by examiner ial application is the U.S. National Phase application# ULTRASOUND SYSTEM AND METHOD FOR BREAST TISSUE IMAGING AND ANNOTATION OF BREAST ULTRASOUND IMAGES This application is the U.S. National Phase application under 35 U.S.C. § 371 of International Application No. PCT/EP2017/063874, filed on Jun. 7, 2017, which claims the benefit of Provisional Application Ser. No. 62/346,641, filed Jun. 7, 2016. These applications are hereby incorporated by reference herein.

BACKGROUND

The present disclosure relates generally to medical imaging systems such as ultrasound imaging systems. An ultrasound imaging system typically includes a user interface which operates in conjunction with a probe to acquire and display images from a subject (e.g., a patient). Acquired images may be displayed, reviewed and/or annotated in real time during the image data acquisition process or offline on an analysis workstation. Medical imaging may be used for screening and diagnostics purposes such as to identify the presence of and/or quantify parameters associated with a tumor in a tissue of the subject. Accurate and early identification and assessment of a tumor may facilitate more effective treatment response. For example in the case of imaging breast tissue, ultrasound imaging has more recently found use in screening and diagnosis of breast cancer. Some patients may present multiple lesions in one or both breast and the accurate and full documentation of all suspicious lesions may facilitate a more effective treatment plan. Thus, tools for more comprehensively and/or efficiently documenting the results of breast ultrasound exams may be desired.

SUMMARY

Examples of ultrasound imaging system and methods for breast tissue imaging are described. An ultrasound imaging system according to one embodiment may include a user interface comprising a display, a processor operatively connected to the user interface, and memory comprising processor-executable instructions, which when executed by the processor cause the user interface to display a first ultrasound image generated from breast imaging data on the display and receive an indication of a first region of interest (ROI) in the first ultrasound image. The memory may include instructions to further cause the user interface to display a second ultrasound image generated from the breast imaging data on the display and receive an indication of a second region of interest in the second ultrasound image. The processor may be configured to determine locations of the first and second regions of interest based on probe position data associated with the first and second images, respectively and cause the user interface to display a visual indication of proximity responsive to a determination that the first and second ROIs meet a proximity condition. For example, the visual indication of proximity may be automatically provided if a relative distance between the first and second ROIs is less than or equal to a predetermined amount or the first and second ROIs are located in a same breast quadrant.

In some examples, the ultrasound imaging system may include a probe and a position sensor attached to the probe. The probe may thus be operatively associated with a position tracking system and the processor further configured to store probe position data with corresponding images acquired with the probe. The probe position data may include information about the spatial location and orientation of the probe. In this manner, the processor may be configured to determine relative distances between any ROIs in any of the images in a data set obtained with the position tracked probe regardless of the orientation of the view planes of the images.

In some examples, the user interface may be configured to display a first ROI indicator and a second ROI indicator corresponding to respective ones of the first and second ROIs on a breast graphic. In such examples, the visual indication of proximity may include changing a look of the first ROI indicator, the second ROI indicator, or both if the relative distance between the first and second ROIs is less than or equal to a predetermined amount or if the first and second ROIs are located in a same quadrant of the breast. In some examples, the user interface may be configured to display a quadrant indicator overlaid on the breast graphic. In some examples, the user interface may be configured to display a distance indicator overlaid on the breast graphic. The distance indicator may be implemented as a line or an elongate rectangle (e.g., a ruler) having a fixed length corresponding to the predetermined amount scaled to the breast graphic. The distance indicator may be movable with respect to the breast graphic such that the user may be able to move the distance indicator next to any of the ROI indicators on the breast graphic. In some examples, the distance indicator may be rotatable responsive to user inputs, such as to align the distance indicator along its length with any two ROI indicators on the breast graphic.

In some examples, the user interface may include a user control for automatically annotating an ultrasound image with ROI location information derived from the probe position data associated with the ultrasound image. In some examples, the processor may be configured to estimate a radial position and a radial distance of an ROI in an image based, in part, on an estimated spatial positon of the nipple of the breast, and wherein the user interface comprises a user control for automatically annotating the image with the radial position and radial distance of the ROI. The estimated spatial location of the nipple of the breast may be obtained by registering the probe with respect to the breast.

A method in accordance with some examples of the present disclosure may include displaying a first ultrasound image of a breast, receiving an indication of a first region of interest (ROI) in the first ultrasound image, and determining a location of the first ROI using probe position data associated with the first ultrasound image. The method may further include displaying a second ultrasound image of the breast, receiving an indication of a second ROI in the second ultrasound image, and determining a location of the second ROI using probe position data associated with the second ultrasound image. The method may further include automatically providing a visual indication of proximity if the relative distance between the first and second regions of interest (ROIs) is less than or equal to a predetermined amount or the first and second ROIs are located in a same quadrant of the breast. In some examples, the first and second images may be acquired contemporaneously such as through multiple sweeps of the breast during the same imaging session. In some examples, the view planes of the first and second images may be angled to one another.

In some examples, the method may include displaying a first ROI indicator on a breast graphic responsive to receiving the indication of the first ROI in the first ultrasound image and displaying a second ROI indicator on the breast graphic responsive to receiving the indication of the second ROI in the second ultrasound image. In such examples, the automatically providing a visual indication of proximity may include automatically changing a look of the first ROI indicator, the second ROI indicator, or both if the relative distance between the first and second regions of interest (ROIs) is less than or equal to a predetermined amount or the first and second ROIs are located in a same quadrant of the breast. In some examples, changing the look of the first ROI indicator, the second ROI indicator, or both may include changing a color, a fill, or a shape of the first ROI indicator, the second ROI indicator, or both. In some examples, the method may further include overlaying a quadrant indicator on the breast graphic.

In some examples, the method may include registering an ultrasound probe with respect to the breast to obtain probe registration position data and dividing a volume of the breast into quadrants based on the probe registration position data. The method may further include associating each of the first and second ROIs with a quadrant based on the location of each of the first and second ROIs within the volume. In some examples, registering the ultrasound probe may include instructing the user to center the probe on the nipple of the breast in a first orientation followed by an orthogonal orientation to obtain the probe registration position data and estimating a spatial location of the nipple of the breast based, in part, on the probe registration position data. In some examples, the method may further include using the spatial location of the nipple to estimate a radial position and a radial distance from the nipple for each of the first and second ROIs. In further examples, the method may include automatically annotating any one of the first image and the second image with the estimated radial position and radial distance of the respective first ROI or second ROI.

The method may further include automatically displaying a distance indicator on the breast graphic adjacent to the first and second ROI indicators if the first and second ROIs are in different quadrants of the breast. In some examples, the method may further include receiving, responsive to user input, an indication to move the distance indicator to a location adjacent one or more other ROI indicators displayed on the breast graphic. The indication to move the distance indicator may include, in some examples, an indication to rotate the distance indicator such as to align the distance indicator with an axis passing through at least two ROI indicators displayed on the breast graphic.

Aspects of the present disclosure, such as certain elements of the user interfaces and/or methods described herein may be embodied in computer-readable media comprising processor-executable instructions. For example, a memory including processor-executable instructions for performing any of the methods described may be included in an ultrasound imaging system according to the present disclosure. In some examples, processor-executable instructions for providing one or more graphical user interfaces or elements thereof may be incorporated into a software package for execution on an analysis workstation. Aspects of the present disclosure may facilitate offline review and analysis of ultrasound images as described further below, however it will be understood that the principles described herein may be equally applied to online image review analysis (e.g., analysis performed on the ultrasound system during or shortly after image acquisition).

DETAILED DESCRIPTION

Figure 1:
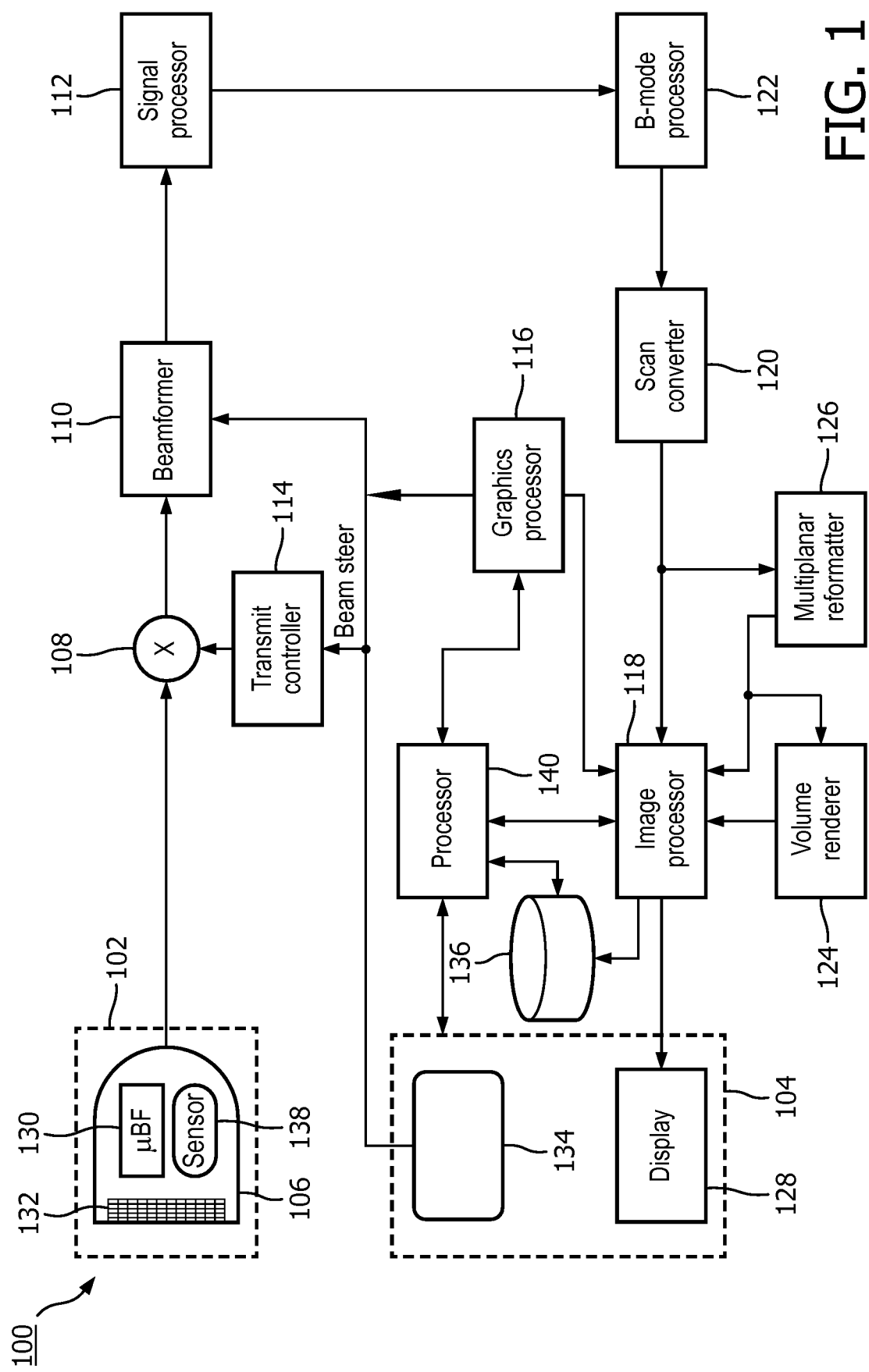
FIG. 1 shows a block diagram of an ultrasound imaging system in accordance with one embodiment.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The use of ultrasound for breast screening, especially in women with mammographically dense breasts, is a rapidly developing trend throughout the world. Breast density is considered one of the strongest predictors of the failure of mammography to detect cancer and is also a well-established predictor of breast cancer risk. Breast imaging with ultrasound, also referred to as breast ultrasound or breast sonography, may be used for initial breast cancer screening as well as for diagnostic or surgical planning purposes. Breast sonography may be performed by an operator, who may or may not be skilled in interpreting ultrasound images. The operator (e.g., ultrasound technician or sonographer) may acquire ultrasound images covering the full breast or a specific portion of the breast. The acquisition of image data may be performed freehand, with or without position tracking, or with some level of automation such as by partially or fully automated control of the movement of the probe. The images may be reviewed online (e.g., on a display of the ultrasound imaging system and/or during the image data acquisition process) or offline (e.g., on an analysis workstation following the image data acquisition process). In some cases, the reading and interpretation of these images may be performed very efficiently off-line by a skilled interpreter (e.g., a radiologist or clinician). Especially when the images are reviewed offline, having a comprehensive set of images, and in some examples accompanied with relevant annotations (e.g., measurements) and position data, may be an important factor in improving the efficiency of the review process.

After the images have been acquired, the skilled interpreter documents the size, location and the number of lesions in each breast. This information is typically included in a report which may aid the surgical team in making treatment decisions. Current techniques for documenting breast lesions involve measurement, typically in two orthogonal planes, such as size of the lesion as well as the location of individual lesions. The location of each lesion may be noted on the ultrasound image and/or in a report with the o'clock position and distance from the nipple. In some cases, additional information and/or measurements for breast lesions may be helpful such as in the case of surgical planning for lesions presenting multifocality or multicentricity. Multifocality and multicentricity (MF/MC) are frequently used descriptors to assess the extent of disease in a patient presenting with breast cancer. The presence of two or more foci of cancer within the same breast quadrant or tumor foci within 5 cm of each other is generally defined as multifocal, while the presence of two or more foci of cancer in different quadrants of the same breast or tumor foci separated by more than 5 cm is generally defined as multicentric. This nomenclature may be used to describe multiple tumors diagnosed clinically on physical examination, on breast imaging studies including mammogram, ultrasound, and magnetic resonance imaging (MRI) or on pathologic analysis. Patients with multifocal breast cancer may be eligible for breast conservation surgery (BCS), provided no other contraindications for this procedure are present), thus it may be desirable to improve the techniques for characterizing multifocality of a suspected tumor.

Currently, unless measurements are made specifically for that reason, it is difficult to extract the information about relative location of the lesions to one another from the images offline. In some cases, a follow-up scan may be required to obtain the additional views that may be needed to obtain relative measurements, which may significantly increase the cost of the ultrasound exam. The present disclosure describes solution which may alleviate some of the problems in this area and/or generally improve the efficiency for characterizing multifocality or multicentricity of breast lesions.

In accordance with the principles of the present invention, an ultrasound imaging system according to one embodiment may include a user interface which includes a display, a processor operatively connected to the user interface, and memory comprising processor-executable instructions, which when executed by the processor to perform functions in accordance with the examples herein. The memory may include instructions which cause the user interface to display a first ultrasound image generated from breast imaging data on the display, receive an indication of a first region of interest (ROI) in the first ultrasound image, display a second image generated from the breast imaging data on the display, and receive an indication of a second ROI in the second ultrasound image, and wherein the processor is configured to determine locations of the first and second regions of interest (ROIs) based on probe position data associated with the first and second images, respectively. The memory may include instructions to automatically provide a visual indication of proximity if a relative distance between the first and second ROIs is less than or equal to a predetermined amount or the first and second ROIs are located in a same breast quadrant. In some examples, the predetermined amount may be the distance that defines multifocality (e.g., 5 cm or a different amount as the definition may change overtime). In other examples, the predetermined amount may be different amount, which may be pre-programmed or user-configurable. In some examples, the first and the second ultrasound images may be ultrasound images generated from imaging data acquired with a position tracked probe and thereby the spatial locations of objects in the images may be readily identifiable based on the probe position data. As such, spatial relationship between objects in the images (e.g., relative distance between two or more ROIs, or a location of an ROI with respect to an anatomical landmark) may be ascertainable based on the position data associated with the imaging data.

Referring now to FIG. 1, an ultrasound imaging system 100 constructed in accordance with the principles of the present invention is shown in block diagram form. The ultrasound imaging system 100 may be used to implement, at least in part, any of the ultrasound imaging systems described herein. FIG. 1 shows ultrasound imaging system 100, which includes ultrasound probe 102, transducer array 132, microbeamformer 130, transmit/receive (T/R) switch 108, beamformer 110, transmit controller 114, signal processor 112, B-mode processor 122, scan converter 120, multiplanar reformatter 126, volume renderer 124, image processor 118, graphics processor 116, user interface 104, input device 134, and output device 128. The components shown in FIG. 1 are merely illustrative, and other variations, including eliminating components, combining components, rearranging components, and substituting components are all contemplated.

In the ultrasound imaging system 100 in FIG. 1, the ultrasound probe 106 includes a transducer array 132 for transmitting ultrasonic waves and receiving echo information. A variety of transducer arrays are well known in the art, e.g., linear arrays, convex arrays or phased arrays. The transducer array 132 for example, can include a two dimensional array of transducer elements capable of scanning in both elevation and azimuth dimensions for 2D and/or 3D imaging. The transducer array 132 is coupled to a microbeamformer 130, typically located in the ultrasound probe 106, which controls transmission and reception of signals by the transducer elements in the array. In this example, the microbeamformer 130 is coupled, such as by a probe cable or wirelessly, to a transmit/receive T/R switch 108, which switches between transmission and reception. The T/R switch 108 may thus protect the beamformer 110 from high energy transmit signals. In some embodiments, the T/R switch 108 and other elements of the system can be included in the transducer probe rather than in a separate ultrasound system base.

The transmission of ultrasonic beams from the transducer array 132 under control of the microbeamformer 130 is directed by the transmit controller 114 coupled to the T/R switch 108 and the beamformer 110. The transmit controller 114 receives input from the user's operation of an input device 134 of user interface 104. The input device 134 may be implemented using a control panel (e.g., a touch screen, a console, or a combination of the two) which may include soft and/or hard controls. One of the functions controlled by the transmit controller 114 is the direction in which beams are steered. Beams may be steered straight ahead from (orthogonal to) the transducer array, or at different angles for a wider field of view. The partially beamformed signals produced by the microbeamformer 130 are coupled to a beamformer 110 where partially beamformed signals from individual patches of transducer elements are combined into a fully beamformed signal.

The beamformed signals may be coupled to a signal processor 112. The signal processor 112 can process the received echo signals in various ways, such as bandpass filtering, decimation, I and Q component separation, and harmonic signal separation. The signal processor 112 may also perform additional signal enhancement such as speckle reduction, signal compounding, and noise elimination. The processed signals may be coupled to a B-mode processor 122, which can employ amplitude detection for the imaging of structures in the body. The signals produced by the B-mode processor may be coupled to a scan converter 30 and a multiplanar reformatter 126. The scan converter 120 arranges the echo signals in the spatial relationship from which they were received in a desired image format. For instance, the scan converter 120 may arrange the echo signal into a two dimensional (2D) sector-shaped format, or a pyramidal three dimensional (3D) image. The multiplanar reformatter 126 can convert echoes which are received from points in a common plane in a volumetric region of the body into an ultrasonic image of that plane, as described in U.S. Pat. No. 6,443,896 (Detmer). A volume renderer 124 converts the echo signals of a 3D data set into a projected 3D image as viewed from a given reference point, e.g., as described in U.S. Pat. No. 6,530,885 (Entrekin et al.) The 2D or 3D images may be coupled from the scan converter 120, multiplanar reformatter 126, and volume renderer 124 to an image processor 118 for further enhancement, buffering and temporary storage for display on an output device 128. The output device 128 may include a display device implemented using a variety of known display technologies, such as LCD, LED, OLED, or plasma display technology.

The graphics processor 116 can generate graphic overlays for display with the ultrasound images. These graphic overlays can contain, e.g., standard identifying information such as patient name, date and time of the image, imaging parameters, and the like. The graphics processor may receive input, such as a typed patient name, from the input device 134. The input device 134 may include one or more mechanical controls, such as buttons, dials, a trackball, a physical keyboard, and others, which may also be referred to herein as hard controls. Alternatively or additionally, the input device 134 may include one or more soft controls, such as buttons, menus, soft keyboard, and other user interface control elements implemented for example using touch-sensitive technology (e.g., resistive, capacitive, or optical touch screens). To that end, the ultrasound imaging system 100 may include a user interface processor (i.e., processor 140), which may control operations of the user interface such as functions associated with soft controls. One or more of the user controls may be co-located on a control panel. For example one or more of the mechanical controls may be provided on a console and/or one or more soft controls may be co-located on a touch screen, which may be attached to or integral with the console.

The ultrasound images and associated graphics overlays may be stored in memory 136, for example for off-line analysis. In some examples, the memory 136 may include local memory provided in the ultrasound system base. In some examples, the memory 136 may include a storage device of a picture archiving and communication system (PACS). In some example, ultrasound images and associated data may be stored both locally and remotely on a PACS server. In addition, the memory 136 may store processor-executable instructions including instructions for performing functions associated with the user interface 104. The user interface 104 can also be coupled to the multiplanar reformatter 126 for selection and control of a display of multiple multiplanar reformatted (MPR) images. In some examples, functionality of two or more of the processing components (e.g., beamformer 110, signal processor 112, B-mode processor 122, scan converter 120, multiplanar reformatter 126, volume renderer 124, image processor 118, graphics processor 116, processor 140, etc.) may be combined into a single processing unit.

In accordance with the examples herein, a sensor 138 may be attached to the ultrasound probe 106 and may be operatively associated with a position tracking system 106 (e.g., an electromagnetic (EM) tracking system), such that the spatial location of the probe can be tracked and/or recorded. The processor 140 may be configured to register the ultrasound probe 106 relative to the subject and determine the spatial location of the probe with respect to a subject based on the registration as well as position data received form the position tracking system 102. The processor may be further configured to associate position data with images acquired with the position tracked probe.

Figure 2:
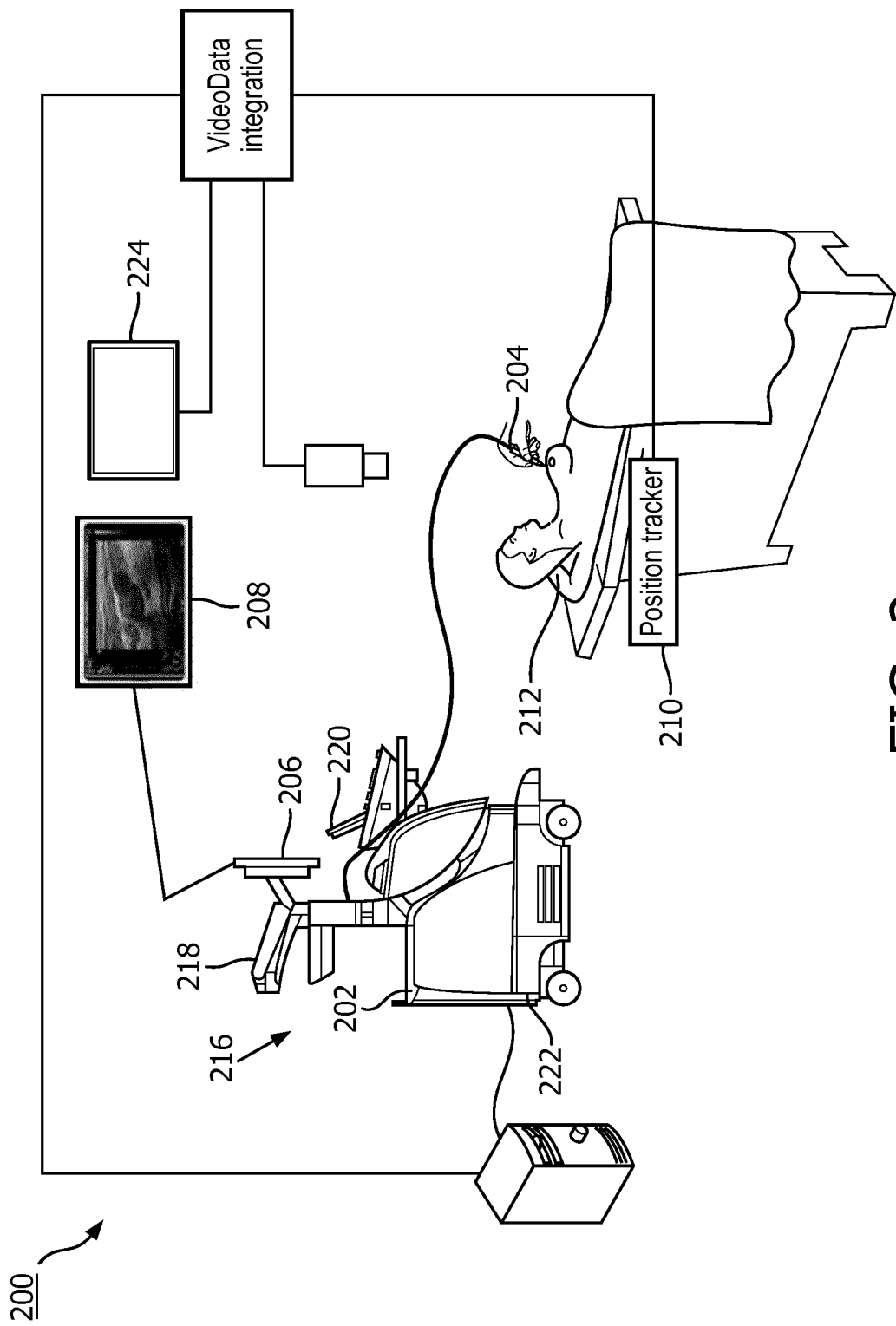
FIG. 2 shows an illustration of an ultrasound imaging system, which may be used to scan breast tissue, for example when performing a freehand breast screening.

FIG. 2 shows an illustration of an ultrasound imaging system which may be used for breast imaging. FIG. 2 shows ultrasound imaging system 200, ultrasound imaging device 202, probe 204, display 206, live image 208, position tracking system 210, patient 212, user interface 216, articulating arm 218, touch screen 220, base 222, and review interface 224. The components shown in FIG. 2 are merely illustrative and other variations, including eliminating components, combining components, rearranging components, and substituting components are all contemplated.

The ultrasound imaging system 200 may include one or more of the components of the ultrasound imaging system 100 in FIG. 1. The ultrasound imaging system 200 may include an ultrasound imaging device 202, which may be a cart-based ultrasound imaging device, a handheld imaging device, or other portable imaging device. For example, one or more of the processing components of the ultrasound imaging device 202 (e.g., beamformer, signal processor, B-mode processor, scan converter, multiplanar reformatter, volume renderer, image processor, graphics processor, and/or other processors which may control various operations of the ultrasound imaging device) may be provided in a base 222, which may be a mobile base. The ultrasound imaging system 200 may include a display 206. The display 206 may be attached to the base 222 via an articulating arm 218 for re-positioning the display 206 such as to allow a displayed image to be viewable by others (e.g., the patient, another ultrasound operator, or a clinician).

The ultrasound imaging device 202 may be connected to a probe 204 via wired (e.g., cable) or wireless (e.g., Wi-Fi) connection. The probe 204 may be used scan breast tissue of a subject (e.g., patient 212). The probe 204 may be configured for freehand operation. By freehand, it is generally meant that the probe is handled (e.g., moved) by an operator (e.g., ultrasound technician) rather than by a machine-controlled actuator. Operation of the probe 204 may be controlled, in part, via the user interface 216. The user interface 216 may include input components, such as mechanical and soft controls, and output components, such as visual, audible and tactile feedback devices. One or more components of the user interface 216 may be implemented using graphical user interface (GUI) elements which may be provided on the display 206, the touch screen 220, or combinations thereof. For example, images (e.g., live image 208) acquired with the probe 204 may be displayed on display 206, on the touch screen 220, or both. The user interface may be configured to provide GUI elements for controlling operations of the ultrasound system. For example, one or more GUI controls may be provided on the touch screen 220.

The user interface 216 may include a review interface 224. The review interface 224 may provide one or more user interface elements to aid the review process and/or improve the documentation and reporting of breast ultrasound results. One or more of the elements of the review interface 224 may be GUI elements, which may be provided on the display 206, the touch screen 220, or a combination thereof. One or more elements of the review interface 224 may be provided in one or more interface windows, concurrently or at different times during the image data acquisition and review processes.

The review interface may include review controls, which may include GUI controls provided on touch screen 220, examples of which will be described further below. In some examples, such as on a conventional workstation, the review controls may be implemented using GUI controls responsive to conventional input devices such as a mouse, trackball, touch pad, keyboard, and the like. The review interface 224 may include graphics which may be displayed on a display of the ultrasound system, on a display of a workstation, or another display. The graphics may be configured to display information (e.g., annotations) in an anatomically intelligent manner, for example by displaying annotations on or next to an anatomically representative graphic (also referred to as body marker). An anatomically representative graphic may include a two-dimensional or a three-dimensional rendering of the anatomical part or organ. As described, the image data may be acquired with a position tracked probe, thus, anatomically intelligent may alternatively or additionally refer to the automatic placement of annotations on a body marker based the probe's position during acquisition of a particular image. In the illustrated example, the anatomically representative graphic may be a breast graphic illustrating a breast side corresponding to the imaged breast. The breast graphic may be overlaid with one or more annotations, as will be further described. Annotations may also be placed next to (e.g., above, below or on any side of the body marker). The annotations (e.g., symbols and/or indicators) may include alphanumeric symbols and/or geometric shapes. In some examples, the graphic may not be anatomically representative and may instead be in the form of a clock diagram, with the annotations overlaid or provided adjacent to the clock diagram.

The ultrasound imaging system 200 may be operatively associated with a position tracking system 210. The position tracking system 210 may be an electromagnetic (EM) tracking system. An EM tracking system typically includes an EM field generator and a sensor. The sensor may be attached to the probe 204 (e.g., embedded in or externally to the housing of the probe 204). In some examples, a tabletop EM field generator may be used. The EM field generator may be movable with respect to a support surface supporting the subject (e.g., an examination table) and thus with respect to the patient. This may enable re-positioning of the EM field generator such that the EM field encompasses the organ or tissue to be scanned (e.g., left breast, right breast). In some examples, the EM field generator may be fixed with respect to the support surface. In other examples, a different type of position tracking system may be used, such as an optical tracking system.

As described, imaging data acquired with a position tracked probe may enable a processor of ultrasound imaging system 200 to determine relative positions of objects within the ultrasound images generated therefrom. For example, the processor of ultrasound imaging system 200 may estimate the spatial location of the probe with respect to the patient 212 using position data from the position tracking system 210, which position data may then facilitate extraction of relevant information from the images acquired with the position tracked probe (e.g., probe 204). The probe position data may include position information about the probe such as the position and orientation of the probe in 3D space. The ultrasound imaging system 200 may enable the user to register the probe 204 with respect to the patient's anatomy. For example, the ultrasound imaging system 200 may be configured to associate the spatial location of the probe when placed at relevant anatomical landmarks (e.g., nipple of the breast, boundaries of the breast, etc.) with the respective landmark. In this manner, the ultrasound imaging system 200 may then be able to calculate relative positions of objects in the images with respect to one or more anatomical landmarks. As a non-limiting example, the ultrasound imaging system 200 may be configured to register the probe with respect to the patient's nipple, such as by marking the location (position and orientation) of the probe when placed vertically and horizontally centered at the nipple. The spatial location of the nipple and/or relative measurements of ROIs to the nipple (e.g., radial position and distance from the nipple) may thus be obtained. The term user may be used interchangeably with operator, which depending on context may, for example, be a sonographer acquiring imaging data, a reviewer reviewing the ultrasound images, a radiologist, a clinician, or another user of the ultrasound imaging system or imaging data acquired therewith.

In some examples, the ultrasound images may be stored in single or multi-frame image files in accordance with a standard format (e.g., DICOM format) appended with the corresponding probe position data. The frames in the image file may be associated with position information such that the spatial location of any object (e.g., an ROI) within each frame may be derived from the position information. A set of images may be acquired through multiple sweeps of the probe 204 along the breast. Typically, the sweeps include angled (e.g., orthogonal) sweeps, and thus, the set of images may include view planes that are angled, in some cases orthogonal, to view planes of other images in the set. With previous systems, in order to obtain relative measurements of multiple lesions, the operator would have needed to acquire a specific view that captures both lesions, such that the measurement can then be made from the ultrasound image. This may slow down the workflow as the operator identifies in real time the two lesions that are to be characterized in relation to one another and then manipulates the probe to obtain the requisite view, or in some cases may require follow-up imaging if the two lesions to be characterized in relation to one another are only identified after the conclusion of the patient's exam. In the examples herein, probe position tracking data may enable easier, faster, and automatic retrieval and relative characterization of suspicious lesions than may have been possible with prior system.

When reviewing the images, a reviewer may display two or more images simultaneously or in sequence and identify regions of interest (ROIs), which may be suspected lesions. For example, the reviewer may identify a first ROI by indicating an approximate center of the first ROI on a first displayed image, such as by placing a cursor and/or clicking on the approximate center of the first ROI. Responsively, the processor may determine a location of the first ROI based on the probe position data associated with the first displayed image. The reviewer may similarly identify a second ROI in a second displayed image, such as by placing a cursor and/or clicking on the approximate center of the first ROI, and the processor may similarly determine a location of the second ROI based on the probe position data associated with the second displayed image. A relative distance between the two ROIs may then be calculated from the locations of each ROI within the same 3D coordinate space, as determined based from the probe position data. In this manner, the system may be configured to automatically determine relative distances between any ROIs in any of the images in the set.

Figure 3:
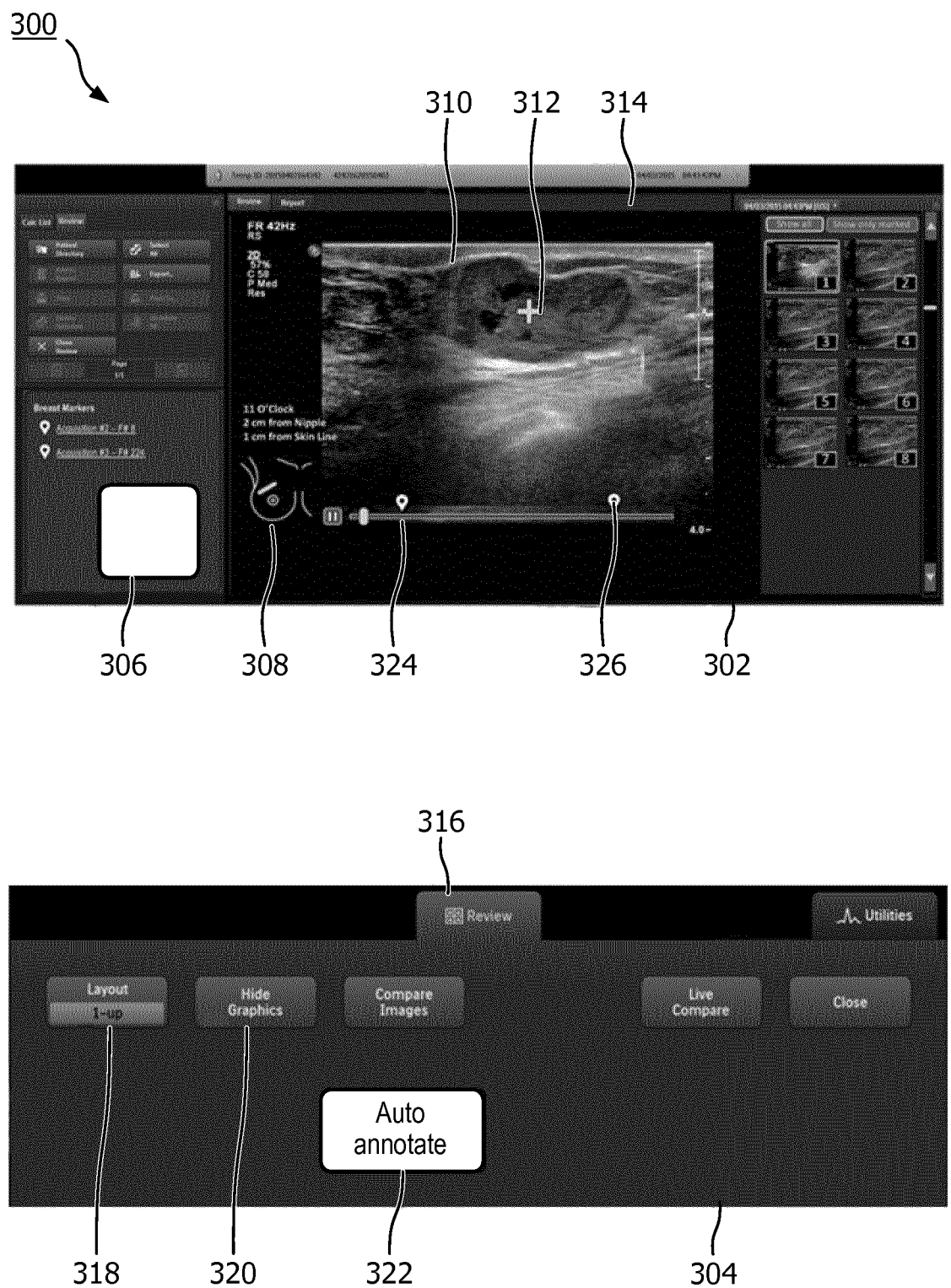
FIG. 3 shows user interface elements in accordance with some examples of the present disclosure.
Figure 4:
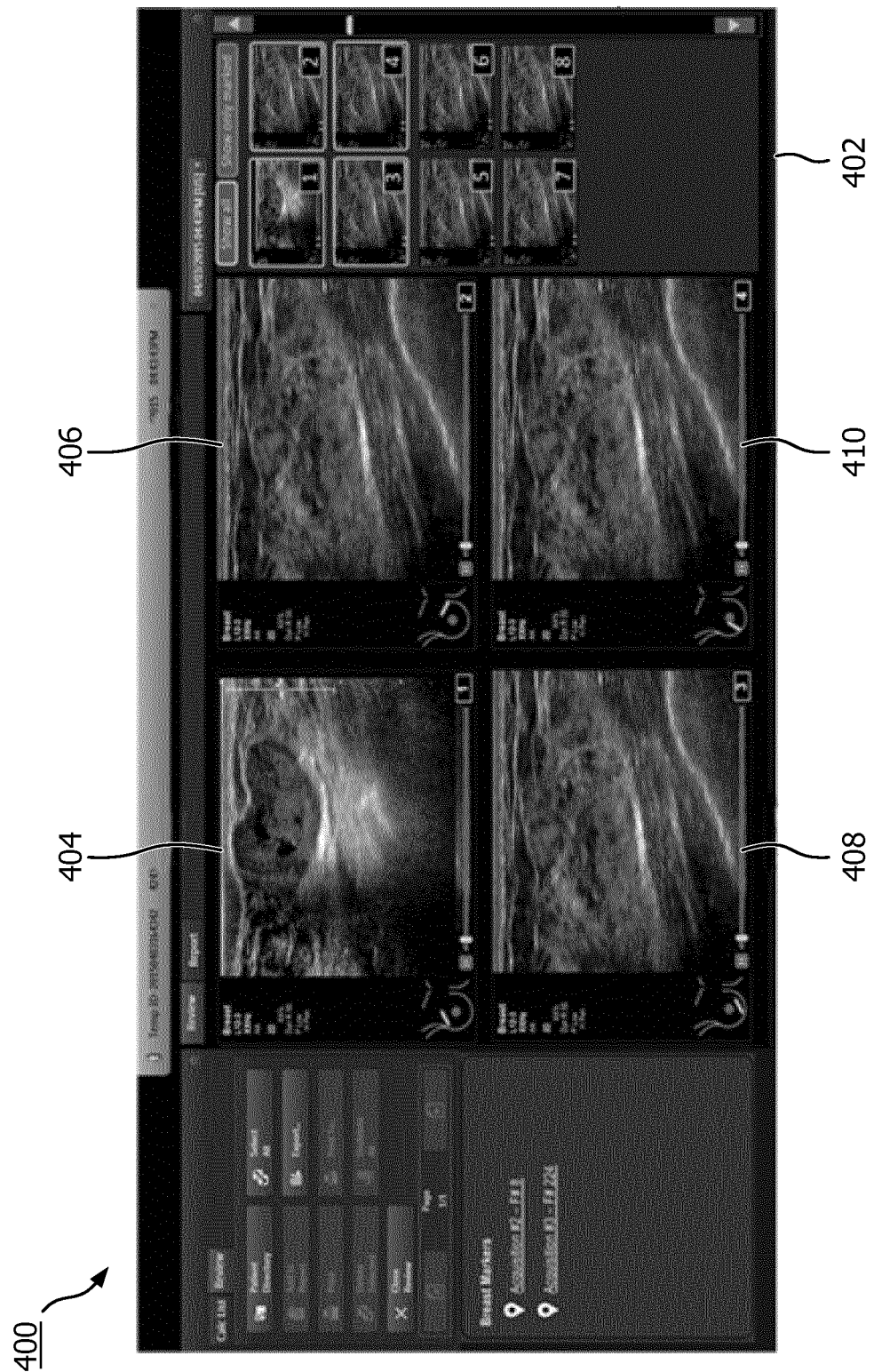
FIG. 4 shows further examples of user interface elements in accordance with the present disclosure.

In accordance with some embodiments, the user interface (e.g., user interface 216) of the ultrasound imaging system may be configured to automatically provide a visual indication of proximity between two ROIs when a condition is met. In some examples, the visual indication of proximity may be provided by displaying a body marker, which is overlaid with relevant ROI information (e.g., one or more ROI indicators, annotations, or other). With reference now also to FIGS. 3 and 4, examples of user interface elements in accordance with the present disclosure are further described. The user interface may be configured to provide a review interface which may include one or more user interface elements for reviewing and/or annotating breast ultrasound images. For example, the review interface may be configured to display a body marker, which in the case of breast ultrasound may be a breast graphic. The breast graphic may provide an illustration of the corresponding breast side that is being imaged and/or characterized, e.g., a right breast graphic may be displayed when imaging or characterizing a right breast and a left breast graphic may be displayed when imaging or characterizing a right breast. In some examples, the breast graphic may provide an illustration of one or more view of the breast being imaged or of both breasts of the patient, which may cumulatively shows the lesions marked as suspicious during the imaging or review process. The body marker may be overlaid with relevant ROI information, such as one or more ROI indicators or annotations associated with individual ROIs or relational information for multiple ROIs.

FIGS. 3 and 4 show user interface elements associated with review interfaces in accordance with some examples herein. FIG. 3 shows review interface 300, first and second interface windows 302 and 304, respectively, first and second body markers 306 and 308, respectively, region of interest 310, cursor 312, and displayed image 314. FIG. 3 also shows review tab 316, layout button 318, graphics button 320, and auto annotate button 322. FIG. 4 shows review interface 400, interface window 402, and first, second, third, and fourth displayed images 404, 406, 408, and 410, respectively. The components shown in FIGS. 3 and 4 are merely illustrative, and other variations, including eliminating components, combining components, rearranging components, and substituting components are all contemplated.

One or more of the elements of the review interface 300 may be displayed on a display of an ultrasound imaging system, such as display 206 or a display of an analysis workstation. One or more of the elements of the review interface 300 may additionally or alternatively be displayed on a touch screen, such as touch screen 220 of ultrasound imaging system 200. Elements of the review interface 300 may be provided concurrently or in sequence and may be arranged in one or more interface windows, such as interface windows 302 and 304. For example, the body markers 306 and 308 may be provided in a first interface window 302 which may be displayed on the display 206. Additionally, the review interface may provide one or more user controls, such as layout, graphics, and auto annotate buttons 318, 320, 322, respectively, which may be provided in a second interface window 304, for example on touch screen 220 of the ultrasound imaging system 200. The specific examples or arrangement of user interface elements is illustrative only and other examples (e.g., hard vs. soft controls) or arrangements of the elements may be employed without departing from the scope of the present disclosure. One or more of the elements of review interface 300 may be used to implement the review interface 224 in the example in FIG. 2.

As described, after the images have been acquired, a user may initiate a review workflow, for example by selecting the review tab 316 of review interface 300. The review tab 316 may provide GUI controls for invoking functions of the review interface. In some examples, the review tab 316 may include a layout button 318, which may enable the user to switch between single image layout (e.g., a 1-up display) to a multi-image layout (e.g., a 2-up display, a 4-up display as shown in FIG. 4, or another layout). As shown in FIG. 4, in a multi-image layout, multiple single or multi-frame image files (e.g., displayed images 404, 406, 408, 410) may be displayed concurrently. A cineloop bar 324 may be displayed with each multi-frame image, which may be used to scroll to a desired frame within a multi-frame image. Bookmarked frames may be indicated on the cineloop bar, for example by providing a bookmark graphic 326 at a corresponding position along the cineloop bar 324. The review interface 300 may include a graphics button 320, which may enable a user to turn on and off the display of one or more graphics, such as the first body marker 306, the second body marker 308, or both. The user interface 300 may include an auto annotate button 322, which may invoke auto annotation functionality of the user interface, as will be further described.

During a review workflow, the user interface may display acquired images in sequence (e.g., in a single image layout as shown in FIG. 3) or concurrently (e.g., in a multi-image layout as shown in FIG. 4). The user interface may receive an indication of one or more regions of interest in one or more of the displayed images responsive to user inputs. For example, a user may identify a suspected lesion by placing a cursor 312 within a region of interest 310 in a displayed image 314. Responsively, a processor (e.g., processor 140 of the ultrasound system 100) may automatically determine the location of each of the marked ROI based, in part, on the probe position data that was stored with the displayed image. The user interface 300 may concurrently display one or more body markers (e.g., a first body marker 306 and/or a second body marker 308) to provide visual feedback during the review process. In the case of breast ultrasound imaging, the body markers 306, 308 may each include a breast graphic overlaid with relevant information, such as information about the marked ROIs, probe information or combinations thereof. The first body marker 306 may be implemented in accordance with any of the examples in FIGS. 6 and 7 described further below, each of which includes a breast graphic overlaid with ROI indicators. The ROI indicators may provide visual indication of the locations of suspected lesions. As more lesions are marked during the review process, corresponding ROI indicators may be added to the body marker 306 to provide a cumulative indication of all of the identified lesions and their locations in the breast. The second body marker 308 may include a breast graphic which is overlaid with a probe indicator showing the position and estimated footprint of the probe used to obtain the any given image frame. The probe indicator may provide a visual indication of the position and orientation of the probe relative to the anatomy of the breast during acquisition of a particular image frame. The probe indicator may be overlaid on a separate body marker from the one used to identify the locations of the lesion. The body marker 308 may be displayed next to the image frame. In some examples the information described with reference to body markers 306 and 308 may be provided on fewer (e.g., a single body marker) or a greater number (three or more) separate body markers.

Figure 5:
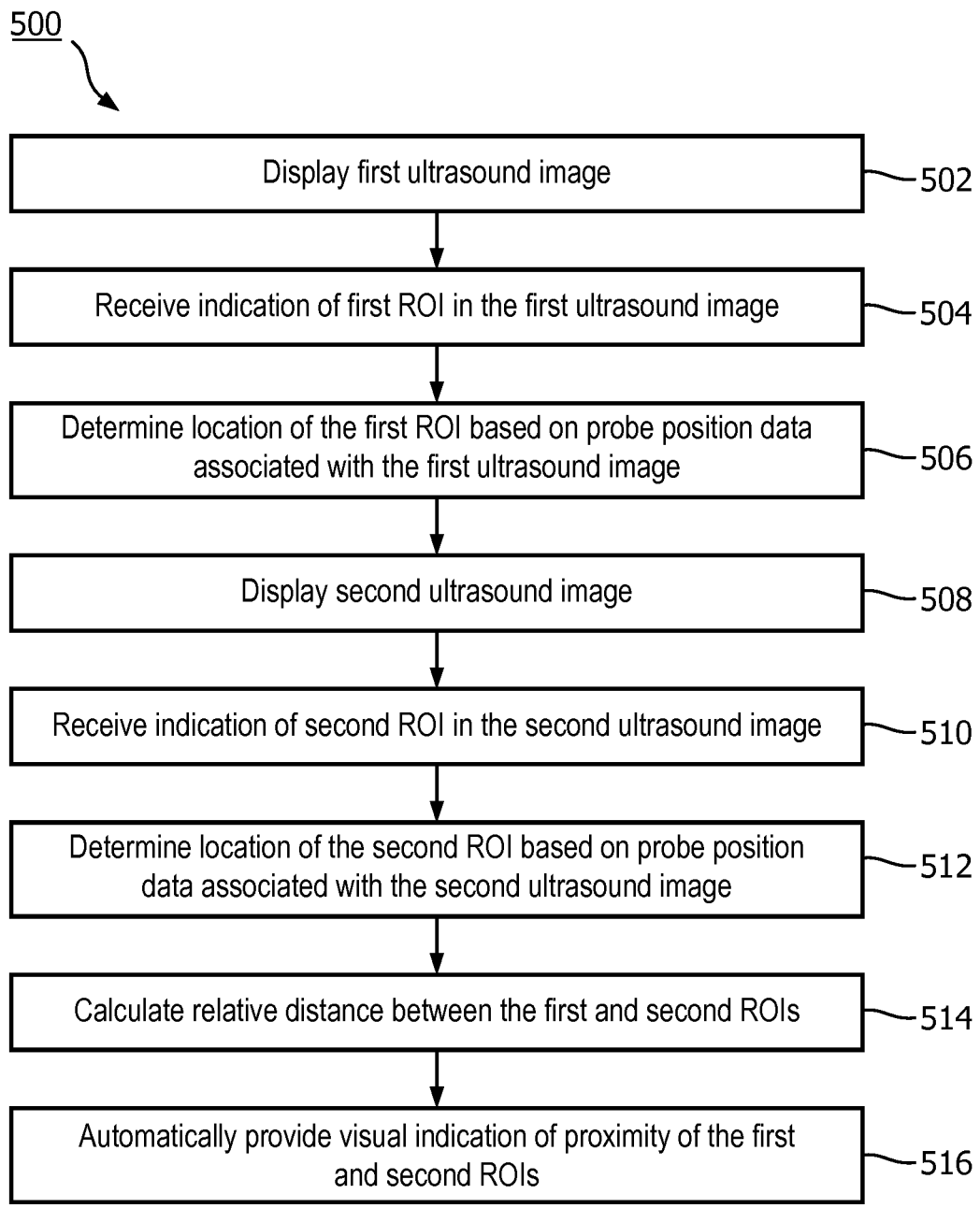
FIG. 5 shows a flow diagram of a process for reviewing breast ultrasound images in accordance with some examples of the present disclosure.
Figure 6:
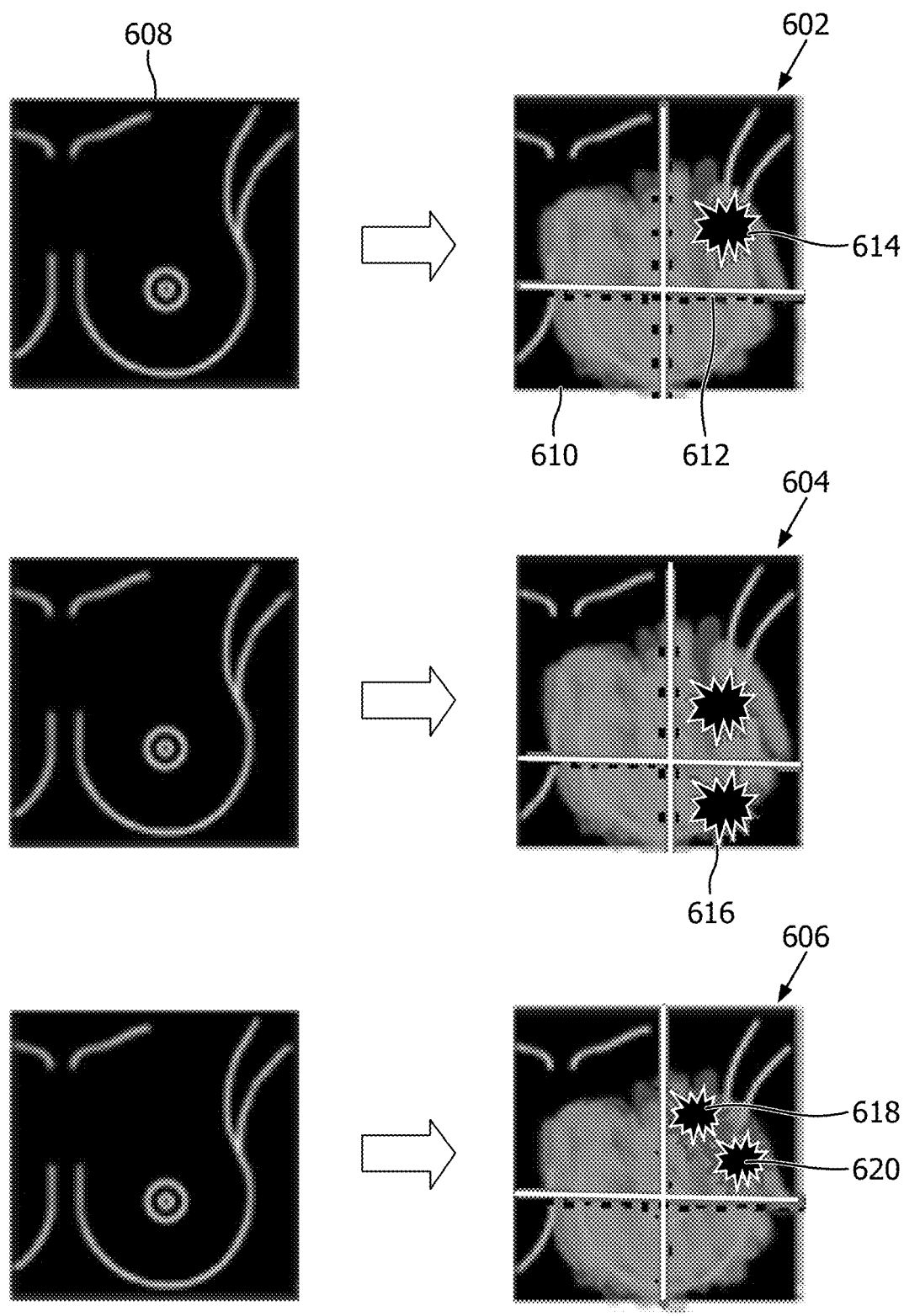
FIG. 6 shows examples of breast graphics in accordance with the present disclosure.
Figure 7:
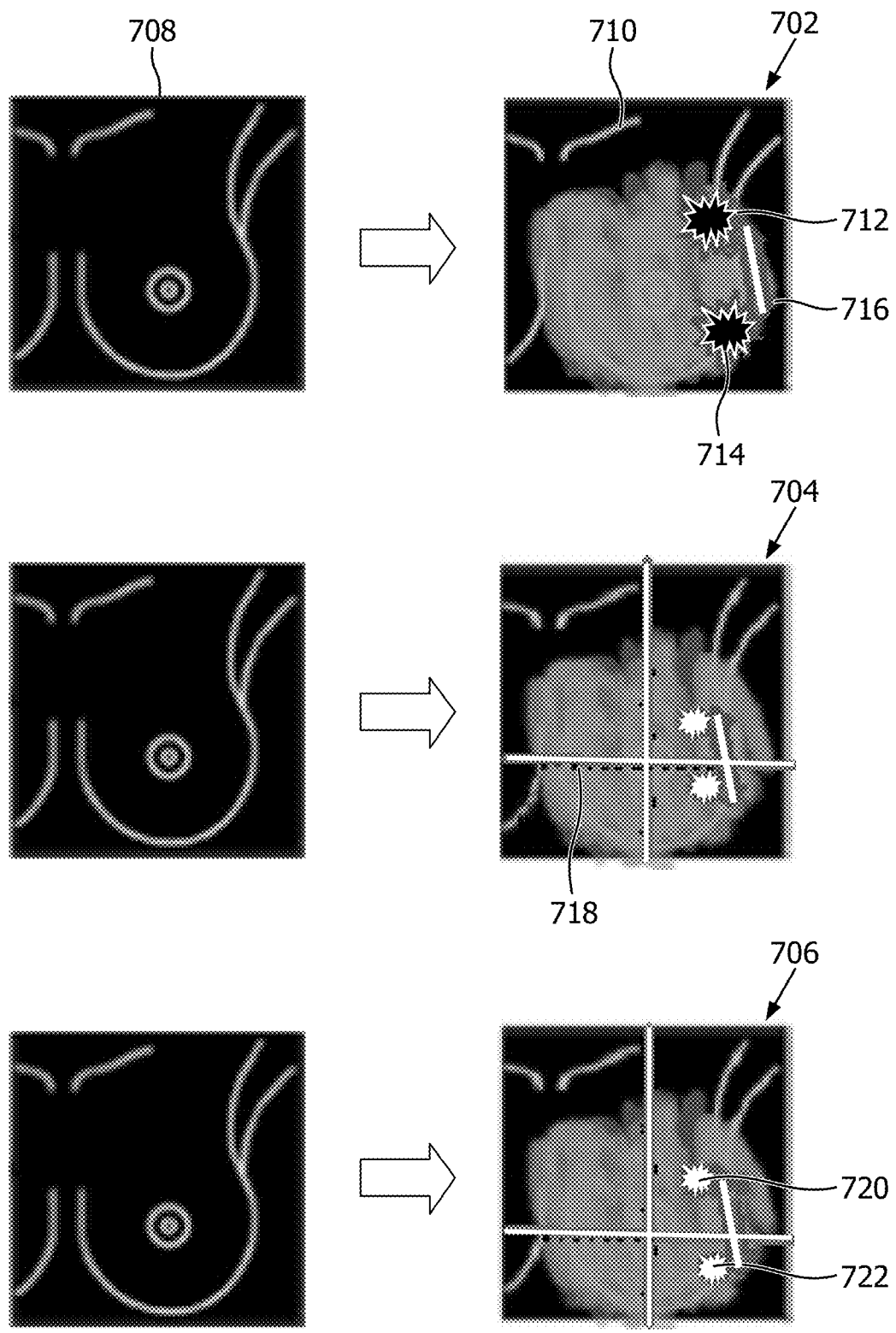
FIG. 7 shows further examples of breast graphics in accordance with the present disclosure.

Referring now also to FIGS. 5-7, examples of processes for reviewing breast ultrasound images are further described. FIG. 5 shows a flow diagram of a process 500 in accordance with some examples. FIGS. 6 and 7 show examples of breast graphics which may be used to implement aspects of the review interface 300. Specifically, FIG. 6 shows blocks 602, 604, and 606 illustrating example breast graphics and FIG. 7 shows blocks 702, 704, and 706 illustrating further examples breast graphics. One or more of the breast graphics in the examples in FIGS. 6 and 7 may be used, in any combination, to implement the body marker 306 in FIG. 3. The components shown in FIGS. 5-7 are merely illustrative, and other variations, including eliminating components, combining components, rearranging components, and substituting components are all contemplated.

The process 500 may begin by initiating a review workflow, such as by selecting the review tab 316. As shown in FIG. 5, the process 500 may include displaying an ultrasound image of an imaged breast, for example as shown in blocks 502 and 508. The first and one or more subsequent ultrasound images may be displayed in an interface window 302 or 402 together or in sequence. As shown in blocks 504 and 510, the system (e.g., processor 140 of ultrasound system 100, or a processor of an analysis workstation) may receive an indication of a first region of interest (ROI) in the first ultrasound image and a second ROI in the second ultrasound image. The indication of the first ROI may be received responsive to the user selecting the first ROI in the first image via a user interface (e.g., responsive to placing cursor 312 within the region of interest 310 in review interface 300), and in similar manner for the second ROI. In some examples, the cursor 312 may be activated automatically upon entry into review mode. In other examples, the cursor 312 may be activated responsive to the user operating a user control, e.g., pressing the auto annotate button 322 or another button of review interface 300. In the latter example, pressing the auto annotate button 322 may launch a cross-hair cursor (as shown in FIG. 3) or another type of cursor and a trackball may be used to control the position of the cursor. When the cursor has been positioned within the region of interest, the user may press a control (e.g., left or right trackball key) to confirm or mark the ROI.

The system may automatically perform certain functions responsive to the marking of an ROI in a displayed image. As shown in blocks 506 and 512, the processor may automatically determine the location of the first ROI and subsequent ROIs, based, at least in part, on probe position data associated with the displayed image. The processor may automatically place annotations on the image responsive to identification of an ROI. For example, the system may automatically annotate the image with the radial position (e.g., o'clock position) and radial distance from the nipple as well as the depth of the lesion (e.g., distance from skin line) estimated based on the position information associated with the displayed image. The annotations may be placed on or proximate the body marker 308 (e.g., as shown in FIG. 3) or elsewhere on the displayed image frame. The annotated image frame may subsequently be stored together with its corresponding annotations and/or included in a report (e.g., a breast study). In some examples, annotation may additionally or alternatively be placed on or proximate the first body marker (e.g., adjacent the corresponding ROI indicator). In yet further examples, each ROI indicator in the body marker 306 may be labeled (e.g., using an alphanumeric character) and the corresponding annotations may be tabulated within a table of the report.

The processor may automatically calculate relative information (e.g., relative distance) for multiple identified ROIs in the images. That is, as multiple image frames are displayed and multiple ROIs are identified, for each subsequent ROI after the first ROI, the system may calculate the relative distance between the subsequent ROIs and any prior ROIs that were identified, as shown in block 514. The relative information may be stored in a database, for example in memory 136. In some examples, the processor may also identify for each ROI, the breast quadrant in which the ROIs is located. For example, through a registration process, the probe may be registered to the patient anatomy such as by marking the nipple with the probe, which may enable the processor to divide a volume of the breast into quadrants. The spatial location of each ROI determined from the probe position data may then be used to assign each ROI to a breast quadrant. The breast quadrant with which each of the ROIs is associated may also be stored in the database.

Concurrently, the system may generate overlays for the body marker 306, which may provide visual indication of the relative ROI information. For example, and referring now also to FIG. 6, at the start of a breast study, the user interface may display a blank anatomically representative graphic (e.g., a breast graphic 608) which may be dynamically updated during the review process. As the user identifies regions of interest on displayed image frames, the user interface may automatically overlay breast graphic 608 with a corresponding ROI indicator (e.g., ROI indicators 614, 616) for each identified ROI to provide an updated breast graphic 610. Updated breast graphics according to some examples are shown on the right hand side of each of the blocks 602, 604 and 606. The ROI indicators may be placed anatomically intelligently on the updated breast graphic 610 in accordance with the respective ROI location determined automatically based on probe position data. With each successive ROI, a corresponding ROI indicator may be added to the breast graphic, such that the body marker 306 may dynamically be updated to provide a cumulative view of all of the ROIs that have been identified during the breast study.

In some examples, the user interface may be configured to overlay a quadrant indicator 612 on the breast graphic as shown in blocks 602, 604, and 606. The quadrant indicator 612 may be displayed at the start of the review workflow, for example concurrently with or shortly after the display of the blank breast graphic 608 or concurrently with the display of the first ROI. In some examples, the quadrant indicator 612 may be automatically displayed responsive to two or more ROIs meeting a proximity condition, such as when two or more ROIs are determined to lie with different quadrants of the breast. In yet further examples, the quadrant indicator 612 may be automatically displayed responsive to two or more ROIs meeting a different proximity condition, such as when two or more ROIs are determined to lie within the same quadrant of the breast. In other examples (e.g., block 702), a quadrant indicator may not be displayed.

As described, the body marker 306 may be configured to automatically provide a visual indication of proximity (see block 516) of two or more identified ROIs, for example by changing a look of one or more ROI indicators. The visual indication of proximity may be provided when a proximity condition is met, such as when a relative distance between two regions of interest (ROIs) is less than or equal to a predetermined amount or when the two ROIs are located in a same quadrant of the breast. In some examples, the predetermined distance may be equal to a distance defining multifocality in breast cancer and thus the indication of proximity may thereby provide an indication of multifocality of a breast cancer tumor. In some examples, the visual indication of proximity may be provided automatically if the two ROIs are within a same quadrant of the imaged breast. In such examples, the process 500 may include steps for determining the quadrant of the breast in which each of the two ROIs is located. In some examples, the processor may cause the shape, the color, and/or the fill of one or both of the ROI indicators corresponding to the ROIs for which the proximity condition is met to automatically change responsive to a determination that the proximity condition has been met.

As shown starting with block 602, a first ROI indicator 614 is overlaid on the breast graphic 608 to provide updated breast graphic 610. As shown in block 604, when a second ROI is identified a corresponding second ROI indicator 616 is overlaid on the updated breast graphic. In the example in block 604, the two ROIs do not meet a proximity condition, and thus no visual indication of proximity is provided. In block 606, a first and second ROI indicators 618 and 620 corresponding to ROIs that meet the proximity condition are displayed as each ROI is identified. Upon determination that the two ROIs meet the proximity condition, the look of one or more of the ROI indicators is automatically changed on the breast graphic, in this case the color of both of the ROI indicators 618 and 620 is changed. As described, the proximity condition may be a relative distance that is less than or equal to a predetermined distance (e.g., 5 cm), location of both ROIs within the same breast quadrant, or both.

Referring now also to FIG. 7, the user interface may be further configured to overlay a distance indicator 716 on the breast graphic. Similar to the examples in FIG. 6, the user interface may initially display a blank breast graphic 708 shown on the left hand side of each of the blocks 702, 704, and 706. The breast graphic may be dynamically updated during the review process to generate an updated breast graphic 710 shown on the right hand side of each of the blocks 702, 704, and 706. As one or more ROIs are identified in accordance with the examples herein, an ROI indicator (e.g., ROI indicators 712, 714, 720, 722) may be placed on the breast graphic. As in the examples in FIG. 6, a quadrant indicator 718 may be displayed, in some examples automatically at the start of the review process or during the review process such as responsive to two or more ROIs meeting a proximity condition. The distance indicator 716 may be displayed additionally or alternatively to a quadrant indicator and/or other visual indications of proximity. For example, block 702 shows updated breast graphic 710 with an overlay of two ROI indicators 712 and 714 and a distance indicator 716 positioned proximate the two ROI indicators 712 and 714. The distance indicator 716 may be displayed automatically on the breast graphic upon determination of two or more ROIs meeting a proximity condition. The distance indicator 716 may have a fixed length corresponding to the predetermined amount (e.g., 5 cm) scaled to the breast graphic. The distance indicator 716 may be automatically displayed proximate (e.g., between) the two ROIs that meet the proximity condition.

In some examples, the distance indicator 716 may be movable, responsive to user input, relative to the breast graphic such that the user may slide the distance indicator 716 to reposition it to any desired location on the breast graphic. In some examples, the distance indicator may be rotatable so as to enable the user to change the orientation of the distance indicator so to enable the user to place the distance indicator between any two ROI indicators on the breast graphic. In this manner the user may use the distance indicator 716 to visually identify lesions that are marked on the breast graphic as meeting a proximity condition. As shown in block 704, the distance indicator may be displayed concurrently with other indicators, such as the quadrant indicator 718, which may be overlaid on the breast graphic in accordance with any of the examples herein. As shown in block 706, the distance indicator and or the quadrant indicator may be displayed in addition to the user interface providing other visual indications of proximity such as changing the look of any of the ROI indicators (e.g., ROI indicators 720 and 722) corresponding with ROIs determined to meet a proximity condition.

Figure 8:
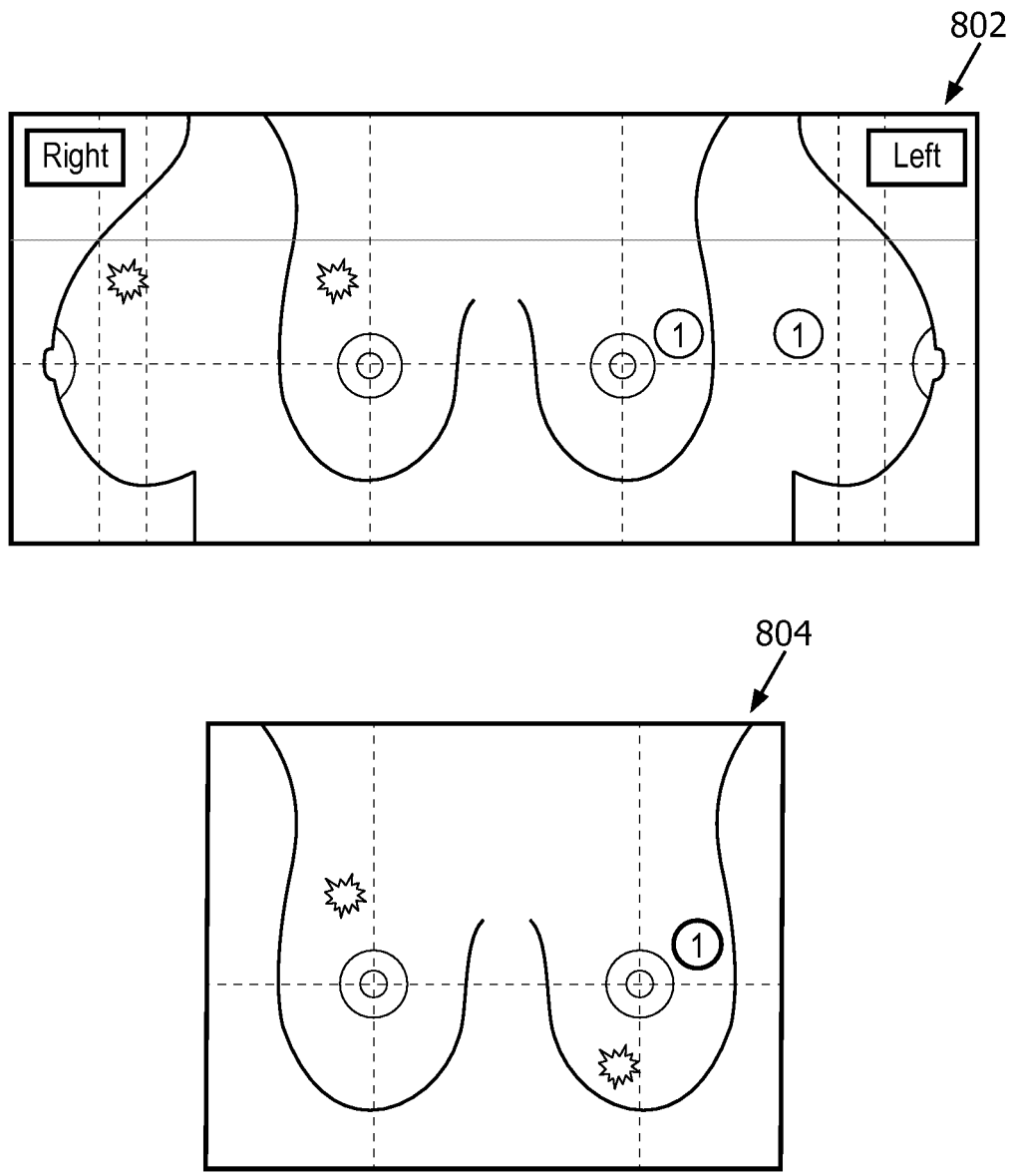
FIG. 8 shows yet further examples of breast graphics in accordance with the present disclosure.

FIG. 8 shows further examples of breast graphics that may be used in accordance with the present disclosure. Any of the examples in FIG. 8 may be used to implement the body marker 306 in FIG. 3 or included in documentation for a breast study. In some examples, the breast graphic may include a plurality of views on a single graphic. For example, the breast graphic may include front and side views of one or both of the left and right breasts (e.g., as shown in block 802), for example when both breasts have been imaged. In some examples, the breast graphic may include front views of both the left and right breasts. In further examples, the breast graphic may include front and side views of only one breast (e.g., the left breast or the right breast), such as when only one breast has been imaged or is part of a study. In these examples, any identified ROIs may be indicated on each relevant view of the multiple views of the breast graphic, such as by including an ROI indicator in the respective relevant view. In the example in block 802, the right breast presents a single lesion which is indicated in both the front and side views of the right breast. The left breast also presents a single lesion, which is similarly indicated on both the front and side views of the left breast. In some examples, a property of presented in a tumor (e.g., malignancy, benignancy, multifocality, etc.) may be indicated with a different ROI indicator, for example, with an indicator having a different shape, color, fill or others. In the example in block 802, the ROI identified in the right breast may have a different property as the ROI identified in the left breast which is shown with a different ROI indicator. In some examples, such as when a cluster of lesions associated with a multifocal tumor are identified, a single ROI indicator of a particular type (e.g., having a particular shape, color or fill may be use) to indicate the whole cluster on the breast graphic. Block 804 shows another example, in which only one view of each breast is shown with the respective ROIs identified in each breast indicated on the relevant view of the breast graphic.

It will be understood that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for breast imaging, the system comprising:
 a user interface comprising a display;
 a processor operatively connected to the user interface; and
 memory comprising processor-executable instructions, which when executed by the processor cause the user interface to:
 display a first ultrasound image generated from breast imaging data on the display;
 receive an indication of a first region of interest in the first ultrasound image;
 display a second ultrasound image generated from the breast imaging data on the display;
 receive an indication of a second region of interest in the second ultrasound image, wherein the processor is configured to determine locations of the first and second regions of interest (ROIs) based on probe position data associated with the first and second images, respectively, wherein the first and second ROIs are associated with a first lesion and a second lesion, respectively; and
 automatically provide a visual indication of proximity if a relative distance between the first and second ROIs is less than or equal to a predetermined amount that indicates multifocality or the first and second ROIs are located in a same breast quadrant.

2. The ultrasound imaging system of claim 1, wherein a view plane of the first ultrasound image is angled relative to a view plane of the second ultrasound image.

3. The ultrasound imaging system of claim 1, wherein the first and second ultrasound images do not overlap or intersect.

4. The ultrasound imaging system of claim 1, wherein the user interface is configured to display a breast graphic and overlay, on the breast graphic, a first ROI indicator corresponding to the first ROI and a second ROI indicator corresponding to the second ROI.

5. The ultrasound imaging system of claim 4, wherein the instructions to automatically provide a visual indication of proximity include instructions to automatically change a look of the first ROI indicator, the second ROI indicator, or both if the relative distance is less than or equal to the predetermined amount or if the first and second ROIs are located in a same breast quadrant.

6. The ultrasound imaging system of claim 4, wherein the instructions to automatically provide a visual indication of proximity include instructions to automatically overlay a quadrant indicator on the breast graphic if the first and second ROIs are located in a same breast quadrant.

7. The ultrasound imaging system of claim 4, wherein user interface is configured to overlay a quadrant indicator on the breast graphic prior to display of the first and second ROI indicators.

8. The ultrasound imaging system of claim 4, wherein the user interface is further configured to overlay a distance indicator on the breast graphic.

9. The ultrasound imaging system of claim 8, wherein the distance indicator has a fixed length corresponding to the predetermined amount scaled to the breast graphic and wherein the distance indicator is movable, responsive to user input, with respect to the breast graphic.

10. The ultrasound imaging system of claim 4, wherein the instructions to automatically provide a visual indication of proximity include instructions to automatically overlay a distance indicator next to the first and second ROI indicators if the relative distance is less than or equal to the predetermined amount.

11. The ultrasound imaging system of claim 1, wherein the user interface comprises an auto-annotate control configured to cause a displayed ultrasound image to be automatically annotated with ROI location information estimated, in part, from probe position data associated with the displayed ultrasound image.

12. The ultrasound imaging system of claim 1, wherein the breast graphic includes a plurality of views of a left breast, a right breast, or combinations thereof, and wherein the first and second ROIs are indicated on each relevant view of the multiple views of the breast graphic.

13. The ultrasound imaging system of claim 1, further comprising a probe configured to transmit ultrasound and receive ultrasound echo for acquiring the breast imaging data, wherein the probe is configured to be operatively associated with a position tracking system for generating the probe position data.

14. The ultrasound imaging system of claim 13, wherein the processor is further configured to spatially register the probe to a nipple of an imaged breast and automatically annotate a displayed ultrasound image with a radial position and a radial distance from the nipple of a region of interest in the displayed ultrasound image.

15. A non-transitory computer-readable medium comprising processor-executable instructions for displaying ultrasound image data on a computing system, which when executed cause the computing system to:
 displaying a first ultrasound image of a breast;
 receiving an indication of a first region of interest (ROI) in the first ultrasound image;
 determining a location of the first ROI using probe position data associated with the first ultrasound image;
 displaying a second ultrasound image of the breast;
 receiving an indication of a second ROI in the second ultrasound image;
 determining a location of the second ROI using probe position data associated with the second ultrasound image; and
 automatically providing a visual indication of proximity if the relative distance between the first and second regions of interest (ROIs) is less than or equal to a predetermined amount that indicates multifocality or the first and second ROIs are located in a same quadrant of the breast, wherein the first and second ROIs are associated with a first lesion and a second lesion, respectively.

16. A method comprising:
 displaying a first ultrasound image of a breast;
 receiving an indication of a first region of interest (ROI) in the first ultrasound image;
 determining a location of the first ROI using probe position data associated with the first ultrasound image;
 displaying a second ultrasound image of the breast;
 receiving an indication of a second ROI in the second ultrasound image;
 determining a location of the second ROI using probe position data associated with the second ultrasound image; and automatically providing a visual indication of proximity if the relative distance between the first and second regions of interest (ROIs) is less than or equal to a predetermined amount that indicates multifocality or the first and second ROIs are located in a same quadrant of the breast, wherein the first and second ROIs are associated with a first lesion and a second lesion, respectively.

17. The method of claim 16, further comprising displaying a first ROI indicator on a breast graphic responsive to receiving the indication of the first ROI in the first ultrasound image, and displaying a second ROI indicator on the breast graphic responsive to receiving the indication of the second ROI in the second ultrasound image.

18. The method of claim 17, wherein the automatically providing a visual indication of proximity comprises automatically changing a look of the first ROI indicator, the second ROI indicator, or both if the relative distance between the first and second regions of interest (ROIs) is less than or equal to a predetermined amount or the first and second ROIs are located in a same quadrant of the breast.

19. The method of claim 18, wherein changing the look of the first ROI indicator, the second ROI indicator, or both may include changing a color, a fill, or a shape of the first ROI indicator, the second ROI indicator, or both.

20. The method of claim 17, further comprising overlaying a quadrant indicator on the breast graphic.

21. The method of claim 17, further comprising:
registering an ultrasound probe with respect to the breast to obtain probe registration position data; and
dividing a volume of the breast into quadrants based on the probe registration position data; and
associating each of the first and second ROIs with a quadrant based on the location of each of the first and second ROIs within the volume.

22. The method of claim 21, further comprising automatically displaying a distance indicator on the breast graphic adjacent to the first and second ROI indicators if the first and second ROIs are in different quadrants of the breast.

23. The method of claim 22, wherein the distance indicator has a fixed length corresponding to the predetermined amount scaled to the breast graphic.

24. The method of claim 23, wherein the distance indicator is movable relative to the first and second ROI indicators, and wherein the method further comprises receiving, responsive to user input, an indication to move the distance indicator to a location adjacent one or more other ROI indicators displayed on the breast graphic.

25. The method of claim 24, wherein the indication to move the distance indicator comprises an indication to rotate the distance indicator to align the distance indicator with an axis passing through at least two ROI indicators displayed on the breast graphic.

26. The method of claim 21, wherein registering the ultrasound probe includes instructing the user to center the probe on the nipple of the breast in a first orientation followed by an orthogonal orientation to obtain the probe registration position data and estimating a spatial location of the nipple of the breast based, in part, on the probe registration position data.

27. The method of claim 26, further comprising using the spatial location of the nipple to estimate a radial position and a radial distance from the nipple for each of the first and second ROIs.

28. The method of claim 27, further comprising automatically annotating any one of the first image and the second image with the estimated radial position and radial distance of the respective first ROI or second ROI.

* * * * *